US005460812A

United States Patent [19]

Sipos

[11] Patent Number: 5,460,812
[45] Date of Patent: * Oct. 24, 1995

[54] COMPOSITIONS OF DIGESTIVE ENZYMES AND SALTS OF BILE ACIDS AND PROCESS FOR PREPARATION THEREOF

[75] Inventor: Tibor Sipos, Lebanon, N.J.

[73] Assignee: Digestive Care Inc., Lebanon, N.J.

[*] Notice: The portion of the term of this patent subsequent to Nov. 9, 2010 has been disclaimed.

[21] Appl. No.: 129,250

[22] Filed: Sep. 29, 1993

Related U.S. Application Data

[60] Continuation-in-part of Ser. No. 104,655, Aug. 11, 1993, Pat. No. 5,324,514, which is a division of Ser. No. 901,734, Jun. 22, 1992, Pat. No. 5,260,074.

[51] Int. Cl.⁶ .......................... A61K 37/48; A61K 37/62; A61K 37/54; A61K 37/547
[52] U.S. Cl. .................. 424/94.1; 424/94.2; 424/94.6; 424/94.64; 424/480; 424/490; 424/497
[58] Field of Search .................... 424/94.1, 94.2, 424/94.6, 94.64, 480, 490, 497

[56] References Cited

U.S. PATENT DOCUMENTS

| Re. 30,910 | 4/1982 | Weigand | 424/238 |
| 3,004,893 | 10/1961 | Martin | 167/73 |
| 3,065,142 | 11/1962 | Antonides | 424/489 |
| 4,011,169 | 3/1977 | Diehl et al. | 435/213 |
| 4,079,125 | 3/1978 | Sipos | 424/32 |
| 4,280,971 | 7/1981 | Wischniewski et al. | 264/15 |
| 4,447,412 | 5/1984 | Bilton | 424/16 |
| 4,828,843 | 5/1989 | Pich et al. | 424/480 |
| 4,944,944 | 7/1990 | Tong et al. | 424/94.6 |
| 5,013,557 | 5/1991 | Tai | 424/493 |
| 5,234,697 | 8/1993 | Sipos | 424/490 |
| 5,262,172 | 11/1993 | Sipos | 424/490 |

FOREIGN PATENT DOCUMENTS

| 1296944 | 11/1972 | United Kingdom. |
| 1362365 | 8/1974 | United Kingdom. |

*Primary Examiner*—Marion C. Knode
*Assistant Examiner*—Kristin Larson

[57] ABSTRACT

Disclosed are gastric acid-resistant polymer-coated buffered digestive enzymes/ursodeoxycholate compositions, process for their preparations and methods of treating digestive disorders, pancreatic enzyme insufficiency, impaired liver function, cystic fibrosis, for regulating the absorption of dietary iron and cholesterol, and for dissolving gallstones by administering the compositions to a mammal in need of such treatment.

10 Claims, No Drawings

1

COMPOSITIONS OF DIGESTIVE ENZYMES AND SALTS OF BILE ACIDS AND PROCESS FOR PREPARATION THEREOF

This Application is a continuation-in-part of application Ser. No. 8/104,655, filed Aug. 11, 1993, now U.S. Pat. No. 5,324,514, which in turn is a divisional of application Ser. No. 07/901,734, filed Jun. 22, 1992 now U.S. Pat. No. 5,260,074 issued as U.S. Pat. No. 5,260,074.

BACKGROUND OF THE INVENTION

1. Field of the Invention

This invention relates to buffered digestive enzymes and salts of bile acids, and more particularly salts of ursodeoxycholic acid compositions for ingestion by a mammal, a process for preparing said compositions, and a method for treating digestive disorders, pancreatic enzyme insufficiency, impaired liver function, pancreatitis, cystic fibrosis, regulating dietary cholesterol absorption and for dissolving gallstones by administering said compositions to a mammal in need of such treatment.

2. Reported Developments

It is known in the prior art that pancreatic enzymes administered to mammals can remedy enzyme deficiency caused by various diseased conditions of the pancreas, such as cystic fibrosis, pancreatitis, pancreatic enzyme deficiency and old age. Oral administration of compositions containing these enzymes requires the presence of certain conditions in order for them to be safe and effective as will be described hereunder.

Pancreatic enzymes produced by the patient's pancreas are released into the duodenum, the pH of which is close to neutral or slightly alkaline. Under these pH conditions the enzymes are active and digestion of the food by the enzymes proceeds normally in the upper segment of the intestine. However, when pancreatic enzymes are administered exogenously to the patient, the gastric conditions in the stomach, namely the presence of acid and pepsin, will irreversibly inactive the enzymes. Therefore, orally administered enzymes must be protected against gastric inactivation so that they remain intact during their transit through the stomach into the duodenum.

Once the exogenously introduced enzymes reach the duodenum, another requirement must be satisfied: the enzymes must be released from their protective environment and intimately mixed with the food transferred from the stomach to effect digestion at a neutral to slightly alkaline condition.

U.S. Pat. No. 4,079,125 incorporated herein by reference, addresses these requirements in a composition containing these enzymes and provides preparative methods for making the compositions. The compositions provided by said patent comprise: an enzyme concentrate in a binder selected from the group consisting of polyvinylpyrrolidone, microcrystalline cellulose, cellulose acetate phthalate, methylcellulose and alginic acid; a stabilizer selected from the group consisting of calcium carbonate, polyvinylpyrrolidone, cellulose acetate phthalate, methylcellulose, starch and modified starches and alginic acid; a disintegrant selected from the group consisting of citric acid, sodium carbonate, sodium bicarbonate, calcium carbonate, starch and modified starches and alginic acid; said mixture is coated with a non-porous, pharmaceutically acceptable enteric coating polymer which is insoluble in the pH range of from about 1.5 to about 5 normally present in gastric fluids, and soluble at a pH of from about 6 to about 9, the normal pH range for mammalian intestinal fluids.

The orally administered composition passes through the stomach while being protected against the acidic environment by its acid-insoluble coating which then disintegrates in the neutral to basic environment of the upper intestine releasing the enzymes from the composition. The process of making the compositions includes the provision of using a solvent and avoiding the presence of water in the blending step of the enzyme/binder/disintegrant, since it is believed that water deactivates some of the enzymes.

Contrary to the teaching of U.S. Pat. No. 4,079,125, it has now been discovered that the complete exclusion of the water (anhydrous condition) during the process of preparing the buffered enzymes/salts of ursodeoxycholic acid compositions in the form of microtablets and microspheres, leads to products that are extremely friable, tend to crumble into pieces upon drying in a fluidized bed dryer or conventional coating pan and disintegrate upon initiation of the polymer coating step. This results in large amounts of dust and agglomeration of the beads into multiplets during the process as well as improper doses of the enzymes upon administration to the patient when quality control fails adequately to sort out and discard rejects.

It is also known that ursodeoxycholic acid (hereinafter UDCA or bile acid) is capable of augmenting liver function, dissolving gallstones and improving the nutritional state of patients having hepatobiliary complications associated with cystic fibrosis. See for example, Ursodeoxycholic Acid Dissolution of Gallstones in Cystic Fibrosis, Sahl, B., Howat, J., Webb, K., *Thorax,* 43:490–1 (1988); Effects of Ursodeoxycholic Acid Therapy for Liver Disease Associated with Cystic Fibrosis, Colombo, C., Setcheil, K. D., Podda, M., Crosignani, A., Roda A., Curcio, L., Ronchi, M. and Giunta, A., *The Journal of Pediatrics,* 117:482–489 (1990); Effects of Ursodeoxycholic Acid Treatment on Nutrition and Liver Function in Patients with Cystic Fibrosis and Longstanding Cholestasis. Cotting, J., Lentze, M. J. and Reichen, J., *Gut* 31:918–921 (1990). Also, UDCA has recently gained acceptance as an effective therapeutic modality to dissolve small to medium size cholesterol gallstones in gallstone afflicted patients. See for example, The Effect of High and Low Doses of Ursodeoxycholic Acid on Gallstone Dissolution in Humans, Salen, G., Colalillo, A., Verga, D., Bagan, E., Tint, G. S. and Shefer, S., *Gastro,,* 78:1412–1418 (1980); Ursodeoxycholic Acid: A Clinical Trial of a Safe and Effective Agent for Dissolving Cholesterol Gallstones, Tint, G. S., Salen, G., Colalillo, A., Graber, D., Verga, D. Speck, J. and Shefer, S., *Annals of Internal Medicine,* 91:1007–1018 (1986); Clinical Perspective on the Treatment of Gallstones with Ursodeoxycholic Acid, Salen, G., *J. Clin. Gastroenterology,* 10 (Suppl. 2):S12–17 (1988); Nonsurgical Treatment of Gallstones, Salen, G. and Tint, G. S., *New England J. Med,* 320:665–66 (1989); and Reducing Cholesterol Levels, Weigand, A. H., U.S. Pat. No. 3,859, 437. The recommended dosage is 10 to 15 mg/kg of body weight. In some patients much higher dosages (for example, about 30 mg/kg of body weight) are required to achieve limited benefits. However, in some patients undesirable side effects (such as, severe diarrhea) seriously limit the use of this drug. The reasons for this wide variation of dosage requirements for therapeutic effectiveness and associated side effects are not completely understood. One hypothesis is that the free acidic form of UDCA is only partially neutralized in the upper intestine to its sodium salt form due to deficiencies in bicarbonate in some of the patients. The residual free acidic (insoluble) form of UDCA is poorly absorbed from the intestine, and a good portion of the administered dosage is excreted intact with feces. When a higher dosage of the acidic form of UDCA is administered to the patient, a large portion of it is neutralized in the distal parts of the intestine which in turn induces diarrhea, a highly undesirable side effect. Also, if the acidic form of UDCA is to be converted into its salt form in the duodenum, it will temporarily exhaust the buffering capacity of the duodenum and it will render the upper intestine partially acidic. The acidic pH impedes the function of the pancreatic enzymes and UDCA cannot emulsify fats and facilitate the hydrolysis of lipids. Furthermore, the many therapeutic benefits derived from the salt forms of UDCA cannot be realized. It should then follow, accordingly, that the salt forms of UDCA should be administered to patients in need of UDCA. U.S. Pat. No. 3,859,437 recommends the administration of a "small but effective amount, sufficient to effect a reduction in the cholesterol level of said human being of the compound 3α 7β-dihydroxy-5β-cholanic acid (UDCA) and the non-toxic pharmaceutically acceptable salts thereof". However, administering the salt form of UDCA to patients has no advantage over the acidic form of UDCA and does not accomplish the desired results since the salt form of UDCA is converted back to the insoluble acidic form of UDCA by gastric acidity. Furthermore, the salt forms, i.e., sodium or potassium, of UDCA are extremely bitter-tasting, and in most patients cause esophageal reflux, nausea and vomiting. Because of these highly undesirable organoleptic and gastric side effects, the salt forms of UDCA has not gained therapeutic utility in the treatment of biliary diseases.

Pancreatic enzymes and salts of UDCA complement one another in the digestive system of a mammal. A dietary supplement containing both the enzymes and salts of UDCA would provide in a convenient predetermined dose the remedy needed to treat the above-described diseased states. However, the acidic form of UDCA is incompatible with pancreatic enzymes. Pancreatic enzymes/UDCA compositions have a pH of about 5 to 5.5. Under these acidic conditions most pancreatic enzymes show a low biological activity of about 10% to 40%. Lipase is especially affected by the low pH for the reasons that: UDCA is only sparingly soluble in aqueous media and is inefficient to emulsify fats; and the acidic UDCA inactivates lipase since lipase requires a basic pH for biological activity.

Pancreatic enzymes/UDCA containing compositions also lack sufficient shelf-life due to the denaturing and detergent effects of UDCA on the pancreatic enzymes. Because of these incompatibilities between UDCA and pancreatic enzymes the many benefits derivable from their combinations could not be realized by the prior art.

It has now been discovered that the problems associated individually with enteric coated microtablets and microspheres containing pancreatic enzymes and compositions containing UDCA, may be overcome in a dietary supplement containing both the pancreatic enzymes and a salt of UDCA. In accordance with the discovery, UDCA is first converted to a pharmaceutically acceptable salt, such as the sodium or potassium salt and then used in a combination with pancreatic enzymes in a composition. Such salts are highly effective to emulsify fats and lipids at a basic pH and facilitate the hydrolysis of the emulsified fat globules. As a result, fat digestion is greatly enhanced. The salts are also more effective than the insoluble acidic form of UDCA to lyse mucus which blocks the intestinal surfaces and prevents absorption of metabolites that results in poor nutrition in cystic fibrosis children.

Pancreatic enzymes then are combined with a salt of UDCA and buffered with a biologically compatible, pharmaceutically acceptable buffer that prevents deactivation of the enzymes and preserves the natural biological activities of both the buffered enzymes and the salt of UDCA. The pancreatic enzymes/salt of UDCA composition can be prepared into microtablets and microspheres in the presence of moisture without inactivation of the enzymes/bile salt composition thereby resulting in products that do not crumble upon drying or disintegrate upon initiation of the polymer coating procedure. The bitter taste and associated gastric disadvantages of UDCA salts are also eliminated by the polymer coating which prevents solubilization of the product in the mouth and stomach of the patient.

Still further, it has been discovered that microspheres in the range of 10 to 80 mesh size (about 2.0 to 0.177 mm range) can be prepared utilizing bile salts as seeds to build up the microspheres. Such small particle size microspheres are especially beneficial for use to treat pancreatic enzymes/bile salt deficiencies in cystic fibrosis children.

SUMMARY OF THE INVENTION

The invention will be described with particular reference to salts of ursodeoxycholic acid, however, it is to be understood that salts of other bile acids such as cholic acid, deoxycholic acid, chenodeoxycholic acid and their glycyl, taurine, methylglycyl and methyltaurine conjugates and salt complexes thereof including their isomers may be used as well.

In accordance with the present invention, buffered digestive enzymes/salt of UDCA compositions are provided which possess desirable characteristics heretofore absent in proposed or existing prior art products.

The buffered digestive enzymes/salt of UDCA is instantly soluble in water, while UDCA alone or in combination with a digestive enzyme is essentially insoluble.

Only the ionized or salt form of UDCA or the conjugated derivatives of UDCA are absorbed from the intestine, while the acidic form of UDCA is insoluble and passes through the intestine intact, unless it is converted to the sodium salt by the intestinal buffers. However, many patients, such as patients with cystic fibrosis, pancreatitis, Billroth I & II diseases and some elderly people, are partially deficient in bicarbonate secretion and lack neutralization capacity to convert the acidic form of UDCA to the sodium salt of UDCA. These patients will only partially benefit from UDCA therapy. The salt of UDCA-containing composition of the present invention overcomes this problem by being instantly soluble in the intestinal juices and absorbable from the intestine. Additionally, the composition also provides extra buffering capacity to neutralize the enteric coating polymer and the acid chyme that is present in the intestine and greatly facilitates the efficient digestion of fats and lipids in the upper intestine.

The buffered digestive enzymes/salt of UDCA composition is microencapsulated and coated with an acid-resistant polymer-coating, which protects the composition from gastric acid and from conversion of the salt of UDCA to the acidic farm of UDCA. The polymer-coated microcapsules are tasteless and the problem associated with the offensive bitter taste of the uncoated acidic form or the uncoated salt of UDCA is thereby alleviated.

The microcapsules uniformly disperse with the food in the stomach and deliver high levels of biologically active buffered digestive enzymes/salts of UDCA into the duodenum. Once in the duodenum, the polymer coating dissolves within about 10 to 30 minutes and the buffered enzymes/salts of UDCA are released to enhance digestion of fats and lipids. As a result, the natural digestive conditions in the intestine are re-established. Epigastric pain, cramps, bloating, flatulence and stool frequency associated with maldigestion of fatty foods are reduced.

Soluble salts of UDCA and conjugated derivatives of UDCA are absorbed more efficiently and in a greater quantity from the intestine than the insoluble acidic form of UDCA, resulting in a more efficient stimulation of the liver enzymes to conjugate ursodiol (UDCA). The increased concentration of the conjugated ursodiol stimulates bile flow, enhances the displacement of toxic bile acid metabolites from the hepatocytes, decreases cholesterol secretion into bile, alters the cholesterol/phospholipid ratio of secreted bile and decreases the absorption of dietary cholesterol from the intestine. The overall result is decreased biliary cholesterol saturation, increased bile flow, dissolution of already formed cholesterol gallstones and protection of the liver from accumulated toxic metabolites.

Most recently, it has also been discovered that the enteric coating polymers employed to protect the pancreatic enzymes against gastric inactivation during gastric transit, are also acidic in nature, and require substantial quantity of base to be neutralized. For example, some of the commercially marketed products, such as CREON®, COTAZYM-S® and PANCREASE® when ground up and dissolved in water had pH's of 5.5, 5.4 and 5.6, respectively. At this acidic pH's, lipase, an essential enzyme that is required by cystic fibrosis patients, is rendered totally ineffective. Therefore, in order to compensate for the acidic nature of the enteric coated polymer, one needs to include extra buffering capacity in the composition to neutralize the acidic enteric coat and provide a basic environment for lipase to exert its enzymatic activity.

Furthermore, recent findings indicate that buffer deficiency is more serious in certain patients than believed heretofore. For example, cystic fibrosis patients are deficient in bicarbonate secretion and their upper intestinal pH's are in the range of 4.5 to 6.5; some of the alcohol induced cholestatic liver diseased patients duodenal pH's are also in the less than neutral range, such as pH 6.0 to 7.6. Even when the pancreas and the gallbladder are maximally stimulated with secretion and cholecystokinin hormones, the intestinal pH's seldom exceed pH 7.0 in cystic fibrosis and 7.6 in alcoholic liver diseased patients.

Because it is difficult to predict the extent of bicarbonate deficiency in these patients population without intubation and collection of intestinal juices for pH and bicarbonate assays, it is necessary to assure that adequate amount of buffer is administered with the exogenous pancreatic enzymes and bile salts compositions.

Accordingly, the composition of the present invention incorporates 5 to 40% w/w of a buffering agent, based on the total weight of the composition, to provide optimal conditions for maximal biological activity of the exogenously administered pancreatic enzymes and bile salts.

The buffered digestive enzymes/salt of UDCA composition for the treatment of enzyme/UDCA deficient mammals comprises a blend of ingredients and a coating therefor expressed in weight per weight percentages based on the total weight of the composition:

a) from about 10 to about 90.0% of a concentrate of an enzyme selected from the group consisting of pancreatin, pancreatic proteases, lipases, nucleases and amylases;

b) from about 0 to about 75%, and preferably of from about 0.3 to about 75% of a UDCA salt in powder form;

c) from about 5 to about 40% of a buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular range of 350 to 50,000 daltons, di-, tri-, and poly-lysine in the molecular range of 290 to 15,000 daltons, diethylamine and triethanolamine;

d) from about 0 to about 16%, and preferably from about 0.9 to about 16% of a disintegrant selected from the group consisting of starch and modified starches, microcrystalline cellulose, and propylene glycol alginate;

e) from about 0.3 to about 15% of an adhesive polymer selected from the group consisting of polyvinylpyrrolidone; microcrystalline cellulose; hydroxypropyl cellulose; cellulose acetate phthalate: and a 60:40 blend of methyl cellulose/hydroxypropyl methyl cellulose; and f) from about 7.0 to about 15% of a non-porous, pharmaceutically acceptable gastric acid-resistant polymer-coating which contains less than 2% talc and which is insoluble in the pH range of from about 1.5 to about 5 but is soluble in the pH range of from about 5.5 to about 9.

The digestive enzymes of the present invention include Pancreatin of multiple strength, pancrelipase, trypsin, chymotrypsin, chymotrypsin B, pancreatopeptidase, carboxypeptidase A, carboxypeptidase B, glycerol ester hydrolase, phospholipase A2, sterol ester hydrolase, ribonuclease, deoxyribonuclease, α-amylase, papain, chymopapain, bromelain, ficin, β-amylase, cellulase, and βgalactosidase (lactase).

The salts of UDCA includes sodium, potassium, ferrous, ammonium, tromethamine, ethanolamine, diethanolamine and triethanolamine salts or salt complexes of UDCA.

In accordance with the present invention, the buffered enzyme/bile salt composition is prepared by a process comprising the steps of:

a) blending dry, powdery ingredients selected from the group consisting of (i) from about 10 to about 90% w/w of an enzyme from the group consisting of pancreatic proteases, lipases, nucleases and amylases; (ii) from about 0 to about 75% w/w, and preferably of from about 0.3 to about 75% of a salt or salt complexes of UDCA selected from the group consisting of sodium, potassium, ferrous, ammonium, tromethamine, ethanolamine, diethanolamine and triethanolamine; (iii) from about 5 to about 40% of a buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane]carbonate), tris-glycine buffer (0.25 mole tris-base and 1.92 mole of glycine, pH 8.3), di-, tri-, and poly-arginine in the molecular range of 350 to 50,000 daltons, di-, tri-, and poly-lysine in the moleculare range of 290 to 15,000 daltons, diethylamine and triethanolamine; (iv) of from about 0 to about 16% w/w, and preferably from about 0.9 to about 16% of a disintegrant selected from the group consisting of starch, modified starches, microcrystalline cellulose and propylene glycol alginate; and (v) from about 0.3% to about 15% w/w of an adhesive polymer selected from the group consisting of polyvinylpyrrolidone, cellulose acetate phthalate, hydroxypropyl cellulose and methylcellulose;

b) wetting said blended ingredients with a liquid to cause the blend to stick together, wherein said liquid is selected from the group consisting of: 1%–25% w/w ethanol/

75%–99% w/w 2-propanol/0.05%–1.5% w/w water; 98%'99% w/w 2-propanol/0.05%–1.5% w/w water; and 1%– 25% w/w methanol/0.05%–1.5% w/w water/ 75%–98% w/w 2 propanol/1%–5% w/w ethylacetate;

c) extruding the liquid-wetted blend through a 10 or a 18 mesh S/S screen;

d) converting the extruded segments to a uniform diameter particle size;

e) compacting the uniform particles to spherical particles;

f) drying the spherical particles;

g) separating the spherical particles if not of uniform size according to desired sizes using U.S. Standard sieve screens;

h) coating the particles with a gastric acid-resistant polymer that dissolves under neutral or slightly basic conditions; and i) drying the polymer-coated spherical particles.

DETAILED DESCRIPTION OF THE INVENTION

In preparing the buffered pancreatic enzymes/bile salt containing microspheres of the present invention utilizing the extrusion, uni-sizer and marumerization process (later described) moisture must be included in the liquid or solvent-adhesive composition to render the adhesive polymer sticky enough to bind the buffered enzymes/bile salt-containing fluffy powder into a pliable, solid mass. This prevents the crumbling of the microspheres during the drying and coating steps as well as allows the preparation of much smaller particle size microspheres, i.e. in the range of 10 to 80 mesh. Accordingly, it was found that the moisture level during the preparation of the composition should be in the range of from about 0.05% w/w to about 1.5% w/w, preferably, in the range of 0.2%w/w to 1.5% w/w, and most preferably in the range of 0.2% w/w to 1.0% w/w. When the compositions contained such amounts of moisture, the microspheres were found to be stable on aging and biological activity was preserved as long as the moisture level did not exceed about 1.5% w/w of the total composition.

Further reference is now made to the process of preparing compositions of the present invention.

The process for the manufacture of microspheres consists of:

1) Blending the dry, powdery ingredients together in a conventional blender and wetting the composition with a suitable liquid composition, hereinbefore described, that causes the dry blend to stick together. The stickiness of the blend can be tested by compressing a handful of the blend in the palm of the hand. If the composition is compressible and sticks together but readily crumbles when squeezed between the fingers, sufficient liquid has been added to the composition for processing in the subsequent granulation step.

2) Extruding the liquid moistened composition through a 10 or a 18 mesh S/S screen using an oscillating/reciprocating granulator or a twin-screw extruder at a medium-to-high speed.

3) Classifying the extruded particles in a so-called "uni-sizer vessel" that rotates at 15 to 45 rpm for about 5 to 10 minutes. (The particles in the "uni-sizer vessel" are converted to a uniform diameter particle size.)

4) Compacting the uniform particles in a marumerizer, (a cylindrical vessel with a rotating disk at the bottom) for about 15 to 70 seconds. An alternative method of compacting the microspheres can also be achieved in a rotating conventional coating pan. In this case, the particles are tumbled in the pan for about 15 to 30 minutes, occasionally wetting the particles with a fine mist of the liquid composition.

5) Drying the spherical particles in an oven under a stream of warm and dry air not exceeding 35° C. and 40% relative humidity.

6) Separating the microspheres according to the desired sizes using U.S. Standard sieve screens.

7) Coating the desired and classified microspheres (for example, in the 16 to 20 mesh and separately in the 30 to 60 mesh size range) with an acid-resistant polymer in fluidized bed coating equipment, or in a conventional coating pan according to standard operating procedures as described in the manufacturer's instruction manual.

8) Drying the polymer coated microspheres in an oven under a stream of warm and dry air not exceeding 35° C. and 40% relative humidity until all the volatile substances (moisture and solvents) are removed.

The following examples will further serve to illustrate the compositions of the present invention wherein the compositions and the process of preparing them will be described with reference to microsphere forms; however, it is to be noted that the microtablet form of the composition and the process of making it is also intended to be covered by the present invention. The process of making the microtablet form of the composition is as follows:

a) blending dry, powdery ingredients selected from the group consisting of (i) from about 10 to about 90% w/w of a digestive enzyme from the group consisting of pancreatic proteases, lipases, nucleases and amylase; (ii) from about 0 to about 70% w/w of a salt of UDCA from the group consisting of sodium, potassium, ferrous, ammonium, tromethamine, ethanolamine, diethanolamine and triethanolamine; (iii) a buffering agent selected from the group consisting of about 5 to about 40% sodium carbonate (anhydrous powder), sodium bicarbonate, potassium carbonate, ammonium carbonate, tromethamine, tris-carbonate (Di[tris(hydroxymethyl)amino-methane]carbonate), tris-glycine buffer (0.25 mole tris-base and 1.92 mole of glycine, pH 8.3), di-, tri-, and poly-arginine in the molecular range of 350 to 50,000 daltons, di-, tri- and poly-lysine in the molecular range of 290 to 15,000 daltons, diethylamine and triethanolamine; (iv) from about 0.3 to about 15% w/w of an adhesive polymer selected from the group consisting of hydroxypropyl cellulose, polyvinylpyrrolidone, cellulose acetate, phthalate, hydroxypropyl cellulose, and methyl cellulose; (v) of from about 0 to about 16% w/w a disintegrant selected from the group consisting of starch, modified starches, microcrystalline cellulose and propylene glycol alginate;

b) wetting said blended ingredients with a liquid to cause the blend to stick together, wherein said liquid is selected from the group consisting of: 1%–25% w/w ethanol/ 75%–99% w/w 2-propanol/0.05%– 1.5% w/w water; 98%–99% w/w 2-propanol/0.05%–1.5% w/w water; and 1%–25% w/w methanol/0.05%–1.5% w/w water/ 75%–98% w/w 2 propanol/1%–5% w/w ethylacetate;

c) granulating or extruding the liquid-wetted blend through a 10 or 18 mesh S/S screen;

d) drying the granulates or extruded particles;

e) admixing a lubricant, such as talc, stearic acid or magnesium stearate in the amount of 0.1 to 2% based on the total weight of the composition with the granulated or extruded particles;

f) compressing the particles into microtablets of an average diameter size of from about 1.0 to about 2.5 mm;

g) coating the microtablets with a gastric acid-resistant polymer that disintegrates under neutral or slightly basic conditions; and h) drying the polymer-coated microtablets.

EXAMPLE I

Generalized Formula Composition (polymer coated)

| Ingredients | % w/w |
| --- | --- |
| Disintegrant | 0–16 |
| Salt of Bile acid | 0–75 |
| Buffering agent | 5.0–40 |
| Enzymes | 0–90 |
| Adhesive Polymer | 0.3–15 |
| Polymer coat/talc mixture | 7.0–15 |

EXAMPLE II

Formula Composition

| Ingredients | IIA (uncoated) % w/w | IIB (coated) % w/w |
| --- | --- | --- |
| Disintegrant | 3.0 | 2.7 |
| Sodium Ursodeoxycholic acid | 5.3 | 4.7 |
| Buffering agent (anhydrous) | 20.0 | 19.9 |
| Enzymes | 70.3 | 60.7 |
| Adhesive Polymer | 1.4 | 1.3 |
| Polymer coat/talc mixture | | 10.7 |

EXAMPLE III

Formula Composition

| Ingredients | IIIA (uncoated) % w/w | IIIB (coated) % w/w |
| --- | --- | --- |
| Disintegrant | 3.0 | 2.6 |
| Sodium-Ursodeoxycholic acid | 70.0 | 60.9 |
| Buffering agent (anhydrous) | 10.0 | 8.7 |
| Enzymes | 10.3 | 9.0 |
| Adhesive Polymer | 6.7 | 5.8 |
| Polymer coat/talc mixture | | 13.0 |

EXAMPLE IV

Formula Composition

| Ingredients | IVA (uncoated) % w/w | IVB (coated) % w/w |
| --- | --- | --- |
| Disintegrant | 2.0 | 1.8 |
| Potassium-Ursodeoxycholic acid | 1.5 | 1.4 |
| Buffering agent (anhydrous) | 8.0 | 7.3 |
| Enzymes | 84.5 | 77.5 |
| Adhesive Polymer | 4.0 | 3.7 |
| Polymer coat/talc mixture | | 8.3 |

EXAMPLE V

Pancreatic Enzyme/Bile Salt Composition

| Ingredients | % w/w |
| --- | --- |
| Bile salt starting seed (20–40 mesh) | 12.8 |
| Disintegrant | 2.3 |
| Buffering agent (anhydrous) | 9.1 |
| Enzymes | 60.0 |
| Adhesive polymer mixture | 5.1 |
| Polymer coat/talc mixture | 10.7 |

The microspheres of Example V were prepared by employing a conventional coating pan. The microspheres were built-up to larger particles sizes by placing the buffered bile salt starting seeds in a rotating coating pan, wetting the microspheres with the liquid/adhesive polymer-containing mixture, followed by slowly dusting the buffered enzyme/disintegrant composition over the tumbling and flowing buffered-bile salt-containing seeds. The above steps were repeated until the seeds were built-up into microspheres having diameters in the range of 10 to 20 mesch, preferably 14 to 16 mesh.

The bile salt starting seeds in Example V were prepared as outlined in Example VII. Suitable bile acids, bile salts and bile acid esters to prepare starting seeds in the particle size range of 20–60 mesh are: Ursodeoxycholic acid; sodium, potassium, ferrous and ammonium salts of ursodeoxycholic acid; ethyl and propyl esters of ursodeoxycholic acid; glycyl and tauroursodeoxycholic acid; sodium, potassium, ferrous and ammonium salts of glycyl and tauroursodeoxycholate; N-methylglycyl ursodeoxycholate and N-methyltauroursodeoxycholate.

TABLE I

Distribution of the Microspheres According to Sizes

| Mesh Size | (mm) | Example IIB Microspheres (%) | Example IIIB Microspheres (%) |
| --- | --- | --- | --- |
| 10 | 2.00 | — | 3.5 |
| 20 | 0.84 | 10.0 | 57.0 |
| 40 | 0.42 | 53.8 | 32.7 |
| 60 | 0.25 | 28.6 | 5.2 |
| 80 | 0.177 | 7.6 | 1.6 |

TABLE II

Moisture Content & Stability of the Microspheres

| Mesh Size | Moisture Content (%) IIB | Stability (4 mo, %)* IIB | Moisture Content (%) IIIB | Stability (4 mo. %)* IIIB |
| --- | --- | --- | --- | --- |
| 20 | 1.1 | 99 | 1.6 | 98 |
| 40 | 0.9 | 98 | 1.9 | 96 |
| 60 | 0.8 | 100 | 2.5 | 95 |
| 80 | 0.9 | 98 | 2.7 | 85 |

*Lipase, Amylase and Protease Activities assayed according to USP XXII.

Preparation of Salts of Bile Acids

In general, a bile acid, such as ursodeoxycholic acid, cholic acid, deoxycholic acid, chenodeoxycholic acid or their glycyl, taurine, methylglycyl and methyltaurine conjugates, was converted to the sodium or potassium salt by dissolving the bile acid in a suitable solvent and titrated with a water soluble alkaline hydroxide, carbonate or bicarbonate solution (e.g. sodium hydroxide, sodium carbonate, sodium bicarbonate, potassium hydroxide, potassium carbonate, potassium bicarbonate solutions) until the pH has reached pH 8.6. The solvent was removed by evaporation or by distillation and the bile-salt was recovered from the media by spray drying or by lyophilizing the remaining solution.

The preparation of the salts of bile acids was illustrated hereunder by the preparation of the salts of ursodeoxycholic acid. It is to be noted, however, that the preparaton of the other salts of bile acids is analogous to the preparation of the salts of ursodeoxycholic acid.

EXAMPLE VI 20 g of UDCA was dissolved in 100 ml of alcohol (methanol, ethanol, isopropanol or an other suitable alcohol that was easily removed after UDCA has been neutralized) and a 10%–30% solution of hydroxide, bicarbonate or carbonate solution of Na or K was added to the reaction mixture, with rigorous mixing. The UDCA solution was titrated until the pH reached 8.6. The alcohol was removed from the reaction mixture on a rotary evaporator, and the aqueous solution was processed to recover the solid Na-UDCA by lyophilization or by spray-drying.

In another modification of preparing salts of UDCA an alcoholic solution of UDCA is mixed with an alcoholic solution of sodium methoxide or sodium ethoxide, followed by evaporation of the alcoholic solvent and precipitation of the Na-UDCA from the concentrated solution by adding the Na-UDCA to ice-cold acetone in a ratio of 1:5 to 1:10. Collecting the NaUDCA crystals by vacuum filtration, washing the crystals with ice-cold acetone followed by air drying the crystals overnight. Example VI(a) illustrates this process.

EXAMPLE VI(a)

1000 g of ursodeoxycholic acid (UDCA) (2.55 mole) is dissolved in 2000 ml of methanol. 500 ml of a methanolic solution of sodium methoxide (NaOCH$_3$) containing 138 g of sodium methoxide (2.55 mole) is then added to the UDCA-containing solution. The so-obtained solution is stirred for one hour to assure complete neutralization. The alcohol is removed from the reaction mixture on a rotary evaporator and the syrupy liquid containing the NaUDCA (500 ml) is added to a rigorously mixed ice-cold acetone (2000 to 5000 ml) solution. The resulting white crystals of NaUDCA are collected by vacuum filtration, washed with ice-cold acetone, followed by air drying the crystals in a tray drier overnight at 40° to 80° C.

EXAMPLE VII

Preparation of Bile Salt Starting Seeds

|  | % w/w |
| --- | --- |
| Bile Salt | 50.0 to 70.0 |
| Disintegrant | 10.0 to 16.0 |
| Buffering agent | 8.0 to 18.0 |
| Adhesive polymer | 12.0 to 16.0 |

The process of making the bile salt-containing starting seeds consisted of: 1) blending the bile salt, disintegrant and the buffering agent together for 10-minutes; 2) spraying the composition with the adhesive polymer mixture until the powdery blend agglomerated; and 3a) extruding the liquid moistened composition through a 10 or 18 mesh S/S screen using an oscillating/reciprocating extruder or a twin-screw extruder; 3b) build-up the granules into microspheres in a fluidized bed unit; or 3c) a rotating pelletizing pan as described in Example V. The subsequent processing steps were the same as outlined in Steps (3) through (6) in the "Detailed Description of the Invention".

EXAMPLE VIII

Buffered Pancreatic Enzyme Formula Composition

| Ingredients | IVA (uncoated) % w/w | IVB (coated) % w/w |
| --- | --- | --- |
| Disintegrant | 0 | 0 |
| Potassium-Ursodeoxycholic acid | 0 | 0 |
| Buffering agent (anhydrous) | 25 | 21.8 |
| Enzymes | 69 | 60 |
| Adhesive Polymer | 6 | 5.2 |
| Polymer coat/talc mixture |  | 13 |

Referring to ingredients used in the above examples:

Suitable Disintegrant in Examples I through V and Example VII are: ECPLOTAB (Mendell, Inc.), microcrystalline cellulose, and propylene glycol alginate (Kelco Co.).

Suitable Buffering Agents in Examples I through V and Examples VII and VIIII are: sodium carbonate (anhydrous powder), sodium bicarbonate, potassium carbonate, and ammonium carbonate, tromethamine, diethanolamine, triethanolamine, tris-carbonate, tris-glycine buffer, di-, tri-, and poly-arginine, di-, tri-, and poly-lysine.

Suitable Enzymes in Examples I through V and Examples VII and VIII are: Pancreation, Pancrelipase and Pancreation concentrates of high potency.

Suitable Bile Salts in Examples I through V and Examples VII and VIII are: sodium, potassium, ferrous and ammonium salts of ursodeoxycholate, glycylursodeoxycholate, taurinoursodeoxycholate, N-methylglycyldeoxycholate and N-methyltauroursodeoxycholate; organic complexes of tromethamine, diethanolamine and triethanolamine of ursodeoxycholate, glycylursodeoxycholate and taurinoursodeoxycholate; N-methylglycylursodeoxycholate; and N-methyltaurinoursodeoxycholate.

Suitable Adhesive Polymeric Agents in Example I through V and Examples VII and VIII are: Hydroxypropyl cellulose (KLUCEL HF, Hercules Co.), polyvinyl pyrrolidone (PLASDONE, GAF Co.), a 60:40 blend of methyl cellulose and ethyl cellulose (Dow Chem. Co.), Hydroxypropyl methyl cellulose (Grades 50 and 55, Eastman Kodak Co.), cellulose acetate phthalate (Eastman Kodak Co.) and propylene glycol alginate (Kelco Co.).

Suitable Acid-Resistant Polymers to coat the microspheres in Example I through V and Examples VII and VIII are: Hydroxypropyl methyl cellulose phthalate, Grades 50 and 55 (Eastman Kodak Co., or Shin-Etsu Chemical Co., Ltd.), AQUATERIC® aqueous enteric coating polymer dispersion (FMC Corp.), EUDRAGIT® acrylic based polymeric dispersion (Rohm Pharma GMBH, Germany), and cellulose acetate phthalate (Eastman Kodak Co.).

Example IX will further illustrate the composition of the acid-resistant polymer-coating:

EXAMPLE IX

| | % w/w |
|---|---|
| Hydroxypropyl methyl cellulose phthalate* | 7.4 |
| Diethyl phthalate or propylene glycol monostearate (MYVEROL P-06) | 2.0 |
| 2-Propanol | 45.2 |
| Ethylacetate | 45.2 |
| Talc, USP | 0.2 |

*When the hydroxypropyl methyl cellulose phthalate was replaced with cellulose acetate phthalate an equally suitable acid-resistant polymer coating was obtained, as long as, talc was also included in the composition. The presence of talc with the film forming polymer caused the deposition of an acid-impermeable polymer coat. When AQUATERIC ® or EUDRAGIT ® aqueous enteric coating polymer dispersion was employed in place of cellulose acetate phthalate (CAP) or hydroxypropyl methyl cellulose phthalate (HPMCP), the microspheres were first sealed with an initial thin layer coating with CAP or HPMCP (2–4% w/w of the microspheres), followed by a secondary coating with an aqueous polymeric latex dispersion (for example, AQUATERIC ® or EUDRAGIT ® ). The employment of the aqueous coating composition as a secondary coating is important to reduce the evaporation of solvents into the atmosphere and thus reduce environmental pollution.

The total amount of the composition required to be administered to a bicarbonate/enzyme/bile salt deficient patient will vary with the severity of the conditions, age and other physical characteristics of the patient. The physicians will prescribe the total amount, the dosage and the frequency of dosage administration on a patient by patient basis. Generally, for enzyme/bile salt deficient patient from about 0.5 to about 1.5 grams of the composition are administered with each major meal, three times a day. Larger amounts may, however, be required for certain conditions, such as for dissolving gallstones.

For ease of administration of the compositions it is preferred to use gelatin capsules containing about 0.2 to 0.5 grams microspheres or microtablets. Gelatin capsules which disintegrate in the acidic environment of the stomach are well-known and utilized in the prior art. Microtablets are of small size, having a diameter between about 1 to 5 mm and a thickness between 0.5 to 4 mm. The microtablet is prepared by conventional tableting procedure. However, the compositions of the present invention in the form of very small particle sizes may be used per se. The microspheres shown in Example IIB and IIIB (Table I) are in the 10 to 80 mesh size range. Table I shows that 100% of the microspheres of Example IIB were in the 20 mesh to 80 mesh size range (0.84 to 0.149 mm) and 89.7% of the coated particles IIIB were in the range of 20 to 40 mesh size range (0.84 to 0.42 mm). Young children or adults with certain diseases are unable to swallow big gelatin capsules. Microspheres of very small size of the present invention could then be administered to the patients with liquid food, such as milk, and apple sauce and with semi-solid foods.

The invention, having been fully described, it will be apparent to one skilled in the art that changes and modifications can be made thereto without departing from the spirit and scope thereof.

What is claimed is:

1. A buffered digestive enzyme/bile salt composition for the treatment of digestive enzyme/bile salt deficiency of mammals comprising, by weight per weight percentages based on the total weight of the composition:

a) from about 10 to about 90.0% of a concentrate of an enzyme selected from the group consisting of pancreatin, pancreatic proteases, pancreatic lipases, pancreatic nucleases and pancreatic amylases;
 b) from about 0.3 to about 75% of a bile salt in powder form;
 c) from 7.3 of a buffering agent selected from the group consisting of anhydrous sodium carbonate, sodium bicarbonate, potassium carbonate, ammonium carbonate, tromethamine, di(tris(hydoxymethyl)aminomethane)carbonate, tris-glycine, di-arginine in the molecular weight range of 350 to 50,000 Daltons, tri-arginine in the molecular weight range of 350 to 50,000 Daltons, poly-arginine in the molecular weight range of 350 to 50,000 Daltons, di-lysine in the molecular weight range of 290 to 15,000 Daltons, tri-lysine in the molecular weight range of 290 to 15,000 Daltons, poly-lysine in the molecular weight range of 290 to 15,000 Daltons, diethylamine and triethanolamine;
 d) from about 0.9 to about 16% of a disintegrant selected from the group consisting of starch, modified starches, microcrystalline cellulose and propylene glycol alginate;
 e) from about 0.3 to about 15.0% of an adhesive polymer selected from the group consisting of hydroxypropyl cellulose, polyvinylpyrrolidone, cellulose acetate phthalate, methyl cellulose and propylene glycol alginate; and
 f) from about 7.0 to about 15% of an non-porous, gastric acid-resistant and pharmaceutically acceptable polymer-coating which contains from about 0.2 to about 2% talc and which is insoluble in the pH range of from about 1.5 to about 5 but is soluble in the pH range of from about 5.5 to about 9.

2. The composition of claim 1 wherein said concentrate of an enzyme is selected from the group consisting of pancreatin, pancrelipase, trypsin, chymotrypsin, chymotrypsin B, pancreatopeptidase. carboxypeptidase A, carboxypeptidase B, glycerol ester hydrolase, phospholipase A2, sterol ester hydrolase, ribonuclease, deoxyribonuclease, α-amylase, papain, chymopapain, bromelain, ficin, β-amylase, cellulase, and β-galactosidase.

3. The composition of claim 1 wherein the buffer component of said buffered digestive enzyme/bile salt is selected from the group consisting of anhydrous sodium carbonate, sodium bicarbonate, potassium carbonate, potassium bicarbonate, ammonium carbonate, tromethamine, tris-carbonate, tris-glycine, di-arginine, tri-arginine, poly-arginine, di-lysine, tri-lysine, poly-lysine, ethanolamine, diethanolamine and triethanolamine.

4. The composition of claim 1 wherein said bile salt is selected from the group consisting of sodium-ursodeoxycholate, sodium glycylursodeoxycholate, potassium-ursodeoxycholate, potassium glycylursodeoxycholate, ferrous-ursodeoxycholate, ferrous glycylursodeoxycholate, ammonium-ursodeoxycholate, ammonium glycylursodeoxycholate, sodium-tauroursodeoxycholate, sodium-N-methylglycylursodeoxycholate, potassium-tauroursodeoxycholate, potassium-N-methylglycylursodeoxycholate, ferrous-tauroursodeoxycholate, ferrous-N-methylglycylursodeoxycholate, ammonium-tauroursodeoxycholate, ammonium-N-methylglycylursodeoxycholate, sodium-N-methyltauroursodeoxycholate, potassium-N-methyltauroursodeoxycholate, ferrous-N-methyltauroursodeoxycholate, ammonium-N-methyltauroursodeoxycholate, sodium-cholate, sodium-deoxycholate, potassium-cholate, potassium-deoxycholate, ferrous-cholate, ferrous-deoxycholate, ammonium-cholate, ammonium-deoxycholate, sodium-chenodeoxycholate, sodium-glycylcholate, potassium-chenodeoxycholate, potassium-glycylcholate, ferrous-chenodeoxycholate, ferrous-glycylcholate, ammonium-chenodeoxycholate, ammonium-glycylcholate, sodium-taurocholate, sodium-N-methylglycylcholate, potassium-taurocholate, potassium-N-methylglycylcholate, ferrous-taurocholate, ferrous-N-methylglycylcholate, ammonium-taurocholate, ammonium-N-methylglycylcholate, sodium-N-methyltaurocholate, sodium-glycyldeoxycholate, potassium-N-methyltaurocholate, potassium-glycyldeoxycholate, ferrous-N-methyltaurocholate, ferrous-glycyldeoxycholate, ammonium-N-methyltaurocholate, ammonium-glycyldeoxycholate, sodium-taurodeoxycholate, sodium-N-methylglycyldeoxycholate, potassium-taurodeoxycholate, potassium-N-methylglycyldeoxycholate, ferrous-taurodeoxycholate, ferrous-N-methylglycyldeoxycholate, ammonium-taurodeoxycholate, ammonium-N-methylglycyldeoxycholate, sodium-N-methyltaurodeoxycholate, sodium-N-methylglycylchenodeoxycholate, potassium-N-methyltaurodeoxycholate, potassium-N-methylglycylchenodeoxycholate, ferrous-N-methyltaurodeoxycholate, ferrous-N-methylglycylchenodeoxycholate, ammonium-N-methyltaurodeoxycholate, ammonium-N-methylglycylchenodeoxycholate, sodium-N-methyltaurochenodeoxycholate, potassium-N-methyltaurochenodeoxycholate, ferrous-N-methyltaurochenodeoxycholate; ammonium-N-methyltaurochenodeoxycholate, ethyl esters of ursodeoxycholate, propyl esters of ursodeoxycholate, sodium-glycylchenodeoxycholate, potassium-glycylchenodeoxycholate, ferrous-glycylchenodeoxycholate, ammonium-glycylchenodeoxycholate, sodium-taurochenodeoxycholate, potassium-taurochenodeoxycholate, ferrous-taurochenodeoxycholate, ammonium-taurochenodeoxycholate.

5. A method for treating digestive enzyme-bile salt deficiency in mammals comprising orally administering an effective amount, sufficient to effect a reduction in digestive enzyme/bile salt deficiency, of the composition of claim 1.

6. The method of claim 5 wherein said treatment is to effect a reduction in digestive enzyme/bile salt deficiency in pancreatic enzyme insufficiency, or impaired liver function, or insufficient absorption of dietary iron and cholesterol, or cystic fibrosis, or presence of gallstones.

7. The method of claim 5 wherein about 0.5 to 1.5 gms of the composition is administered to a digestive enzyme/bile salt deficient patient with each meal three times a day.

8. The method of claim 7 wherein said composition is administered in an acid soluble capsule containing from about 0.2 to about 0.5 grams of microspheres or microtablets.

9. The method of claim 7 wherein said composition is administered admixed with a liquid or a semi-solid food.

10. The method of claim 5 wherein said treatment is to effect a reduction in digestive enzyme/bile salt deficiency in digestive disorders.

* * * * *